United States Patent [19]

Masaki

[11] Patent Number: 4,528,194

[45] Date of Patent: Jul. 9, 1985

[54] 2-(4-DIPHENYLMETHYLPIPERAZINYL)-1-PHENYL ALKANOL OR THEIR SALTS, A PROCESS FOR THEIR PRODUCTION AND A CEREBRAL CIRCULATION-IMPROVING DRUG

[75] Inventor: Mitsuo Masaki, Chiba, Japan

[73] Assignee: Nippon Chemiphar Co., Ltd., Tokyo, Japan

[21] Appl. No.: 513,093

[22] Filed: Jul. 12, 1983

[30] Foreign Application Priority Data

Dec. 2, 1982 [JP] Japan .................. 57-212036

[51] Int. Cl.³ .................. A61K 31/495; C07D 241/04
[52] U.S. Cl. .................. 514/255; 544/396
[58] Field of Search .................. 544/396; 424/250

[56] References Cited

U.S. PATENT DOCUMENTS 3,505,334  4/1970  Regnier et al. .................. 544/396
3,868,377  2/1975  Raabe et al. .................. 544/396

FOREIGN PATENT DOCUMENTS 2111776  10/1971  Fed. Rep. of Germany ...... 544/396
   4087   1/1975  Japan .................. 544/396

OTHER PUBLICATIONS

Raynaud et al, Chem. Abst., vol. 74, 1971, p. 318, 22882u.

Primary Examiner—Donald G. Daus
Assistant Examiner—Cecilia Shen
Attorney, Agent, or Firm—Oblon, Fisher, Spivak, McClelland & Maier

[57] ABSTRACT

A piperazine derivative of the formula:

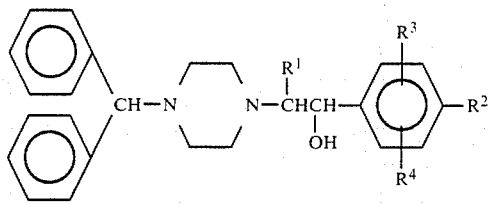

wherein $R^1$ is a hydrogen atom or a lower alkyl group; $R^2$ is a hydroxyl group, an aralkyloxy group, a lower alkoxy group containing 1-5 carbon atoms or a lower alkenyloxy group containing 3-5 carbon atoms; $R^3$ is a hydrogen atom, or an aralkyloxy group, a lower alkoxy group containing 1-5 carbon atoms or a lower alkenyloxy group containing 3-5 carbon atoms; and $R^4$ is a hydrogen atom or a lower alkoxy group containing 1-5 carbon atoms, provided that $R^2$ is a group other than the lower alkoxy group containing 1-5 carbon atoms when both $R^3$ and $R^4$ are hydrogen atoms; or a pharmaceutically acceptable salt is effectively useful as a cerebral circulation-improving agent.

5 Claims, No Drawings

2-(4-DIPHENYLMETHYLPIPERAZINYL)-1-PHENYL ALKANOL OR THEIR SALTS, A PROCESS FOR THEIR PRODUCTION AND A CEREBRAL CIRCULATION-IMPROVING DRUG

BACKGROUND OF THE INVENTION

1. Field of the Invention

This invention relates to novel piperazine derivatives or pharmaceutically acceptable salts thereof and more particularly to such a piperazine derivative represented by the following formula (I):

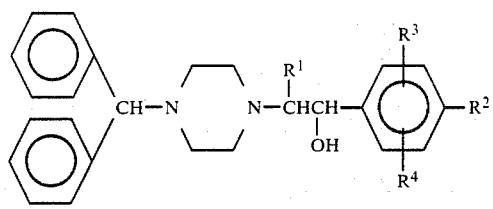

wherein $R^1$ is a hydrogen atom or a lower alkyl group; $R^2$ is a hydroxyl group, an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^2$ is a group other than the lower alkoxy group containing 1–5 carbon atoms when both $R^3$ and $R^4$ are hydrogen atoms; or a pharmaceutically acceptable salt thereof.

Further, the invention is concerned with a process for preparing such derivative or ester and with a cerebral circulation-improving drug containing the same.

2. Description of the Prior Art

Glucose and oxygen, which are energy sources required for the activation of brain cells, are principally supplied by means of blood. Any disorder or ailment would occur when cerebral blood flow is suspended even for several seconds. For example, a thrombus which has formed in a cerebral vessel reduces the cerebral blood flow and hence induces cerebral apoplexy or the like. It has also been known that coagulation of platelets takes place in the course of thrombus formation.

Thus, in the last several years, there has been increased emphasis on the development of a medicine which could exhibit both a blood flow increasing effect and a platelet anti-coagulating effect so as to prevent or cure cerebral circulation insufficiency or failure.

The present inventor has carried out extensive research with a view toward developing such a medicine. As a result, it has been found that piperazine derivatives represented by the formula (I) above or salts thereof are effective to selectively vasodilate peripheral vessels, particularly at vertebrae, in increasing blood flow and suppressing platelet coagulation.

As prior art compounds structurally similar to the piperazine derivatives (I) of the present invention, there have been known 2-(4-diphenylmethylpiperazinyl)-1-phenylethanol [Sv. Zikolova and A. Florin, Tr. Nauchnoissled. Khim.-Farm. Inst., 8, 89–100 (1972)] and 2-(4-diphenylmethylpiperazinyl)-1-methyl-1-phenylethanol (Delalande S. A., Ger. Offen., 2,111,776). Both of the compounds are represented by the following formula (VII):

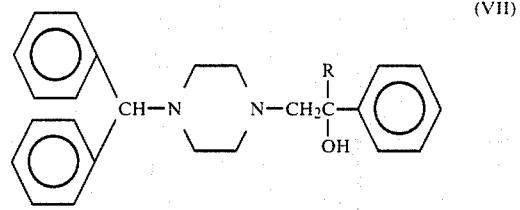

wherein R is a hydrogen atom or a methyl group.

However, these publications are silent as to how the prior art compounds would exert an improved effect on celebral circulation. It has been confirmed from some tests conducted by the inventor that such compounds are only marginal in their vasodilating activity for peripheral vessels, as will be described hereinafter. Of noteworthy importance is the fact that the desired vasodilating effects for peripheral vessels are attributable to a specific configuration in which the piperazine derivative of the formula (I) has either one of hydroxy, aralkyloxy, lower alkoxy and lower alkenyloxy groups at the 4-position of the benzene ring of the phenethyl moiety. The present invention is based upon this discovery.

SUMMARY OF THE INVENTION

Accordingly, it is an object of the invention to provide a novel piperazine derivative of the formula (I) or a pharmaceutically acceptable salt thereof which is free of the above-noted difficulties and which is effectively useful as a pharmaceutical product.

Another object of the invention is to provide a novel process for the preparation of such compound or salt.

A further object of the invention is to provide a cerebral circulation-improving drug which contains such compound or salt as the effective component.

According to one aspect of the invention, there is provided a piperazine derivative represented by the following formula (I):

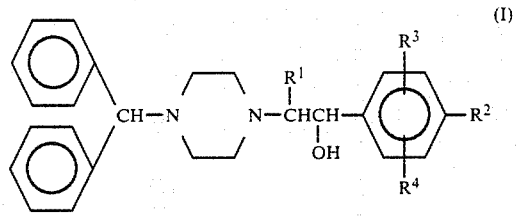

wherein $R^1$ is a hydrogen atom or a lower alkyl group; $R^2$ is a hydroxyl group, an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^2$ is a group other than the lower alkoxy group containing 1–5 carbon atoms when both $R^3$ and $R^4$ are hydrogen atoms; or a pharmaceutically acceptable salt thereof.

According to another aspect of the invention, there is provided a process for preparing a piperazine derivative represented by the following formula (I):

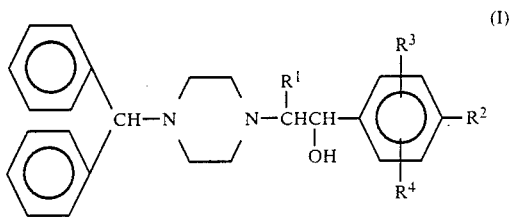

(I)

wherein $R^1$ is a hydrogen atom or a lower alkyl group; $R^2$ is a hydroxyl group, an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^2$ is a group other than the lower alkoxy group containing 1–5 carbon atoms when both $R^3$ and $R^4$ are hydrogen atoms; or a pharmaceutically acceptable salt thereof, which process comprises reducing a compound represented by the following formula (II):

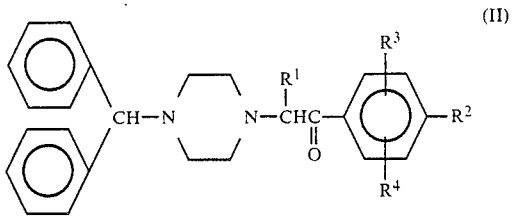

(II)

where $R^1$, $R^2$, $R^3$ and $R^4$ have the same significance as defined above; and if desired, converting the piperazine derivative to the corresponding salt by a method known per se in the art.

According to a further aspect of the invention, there is provided a process for preparing a piperazine derivative represented by the following formula (I'):

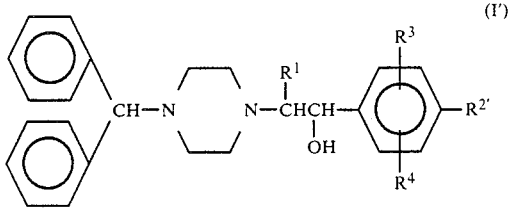

(I')

wherein $R^1$ is a hydrogen atom or a lower alkyl group; $R^{2'}$ is an aralkyloxy group, a lower alkoxy group containing 1–5 carbon atoms or a lower alkenyloxy group containing 3–5 carbon atoms; $R^3$ is a hydrogen atom, or an aralkyloxy group, or a lower alkoxy group containing 1–5 carbon atoms or a lower alkeneloxy group containing 3–5 carbon atoms; and $R^4$ is a hydrogen atom or a lower alkoxy group containing 1–5 carbon atoms, provided that $R^{2'}$ is a group other than the lower alkoxy group containing 1–5 carbon atoms when both $R^3$ and $R^4$ are hydrogen atoms; or a pharmaceutically acceptable salt thereof, which process comprises reacting a compound represented by the following formula (III):

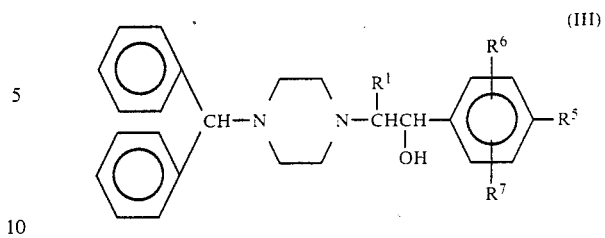

(III)

wherein $R^1$ is a hydrogen atom or a lower alkyl group; $R^5$ is a hydroxyl group, an aralkyloxy group, a lower alkoxy group containing 1–5 carbon atoms or a lower alkenyloxy group containing 3–5 carbon atoms; $R^6$ is a hydrogen atom, or a hydroxyl group, an aralkyloxy group, a lower alkoxy group containing 1–5 carbon atoms or a lower alkenyloxy group containing 3–5 carbon atoms; and $R^7$ is a hydrogen atom, or a hydroxyl group or a lower alkoxy group containing 1–5 carbon atoms, provided that at least one of $R^5$, $R^6$ and $R^7$ is a hydroxyl group, with a compound represented by the following formula (IV):

$R^8$—X (IV)

wherein $R^8$ is an aralkyl group, a lower alkyl group containing 1–5 carbon atoms or a lower alkenyl group containing 3–5 carbon atoms; and X is a reactive group; and if desired, converting the piperazine derivative to the corresponding salt by a method known per se in the art.

According to a still further aspect of the invention, there is provided a cerebral circulation-improving drug comprising as the effective component a piperazine derivative represented by the following formula (I):

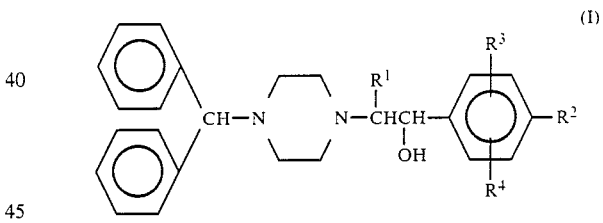

(I)

wherein $R^1$ is a hydrogen atom or a lower alkyl group; $R^2$ is a hydroxyl group, an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^2$ is a group other than the lower alkoxy group containing 1–5 carbon atoms when both $R^3$ and $R^4$ are hydrogen atoms; or a pharmaceutically acceptable salt thereof.

DETAILED DESCRIPTION OF THE PREFERRED EMBODIMENTS

In the piperazine derivatives of the formula (I), suitable "lower alkyl" groups for the substituent $R^1$ include, for exmaple, methyl, ethyl, n-propyl, iso-propyl and like groups. Suitable "lower alkoxy" groups for each of $R^2$, $R^3$ and $R^4$ include, for example, methoxy, ethoxy, n-propyloxy and like groups. Suitable "lower alkenyloxy" groups for each of $R^2$ and $R^3$ include, for example, propenyloxy, isopropenyloxy, allyloxy and like groups. Suitable "aralkyloxy" groups for each of $R^2$ and $R^3$ include, for example, benzyloxy, phenethyloxy, p-methoxybenzyloxy and like groups.

The compound (I) of the invention may be prepared, for example, by reducing its corresponding carbonyl compound of the formula (II) in accordance with the following reaction scheme:

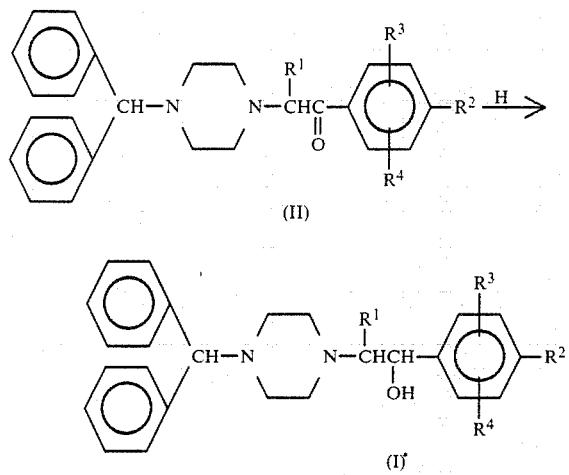

wherein $R^1$, $R^2$, $R^3$ and $R^4$ have the same significance as defined above.

The compound (II) which is useful as a raw material in the practice of the invention may be prepared, for example, by reacting 1-diphenylmethylpiperazine of the formula (V) with an acetophenone derivative of the formula (VI) in accordance with the following reaction scheme:

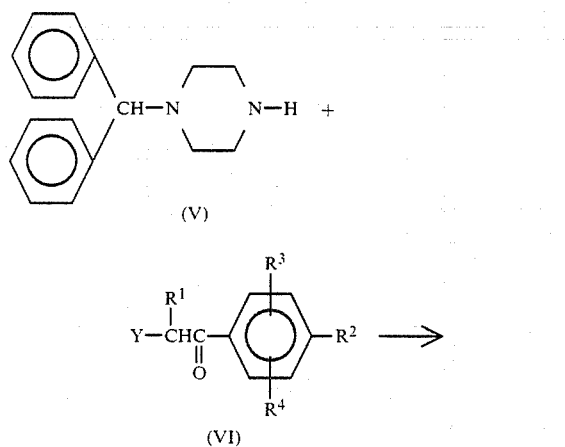

wherein Y is a halogen atom, and $R^1$, $R^2$, $R^3$ and $R^4$ have the same significance as defined above.

In the above reaction, the substituent $R^2$ in the formula (VI) may be protected in advance by a commonly used protecting group such as a benzyl group when the substituent is a hydroxyl group. The reaction may be effected in the presence of a basic catalyst.

In order to effect the reduction reaction by the process of the invention, either one of the following reaction techniques may be employed:

(1) Reduction by a metal hydride complex compound such as sodium borohydride, lithium aluminum hydride, zinc borohydride, lithium borohydride or the like (2) Reduction by a diborane or substituted borane (3) Catalytic reduction in a hydrogen gas atmosphere at normal pressure or at an elevated pressure ranging from several to several tens of atms using a catalyst such as copper, cobalt, nickel, palladium, palladium-carbon, platinum, platinum oxide, rhodium or the like (4) Reduction by a metal and an acid, for example, by iron and acetic acid, zinc and hydrochloric acid, formic acid and acetic acid, or a like combination (5) Reduction by a metal and an alkali, for example, by zinc and sodium hydroxide (6) Meerwein-Ponndorf reduction using aluminum isopropoxide or aluminum ethoxide (7) Reduction by an alcohol and a metal such as sodium Any reaction solvent may be used so long as it does not adversely affect raw materials and reduction. Eligible solvents are ethers such as tetrahydrofuran and diethyl ether; alcohols such as methanol and ethanol; acids such as acetic acid and hydrochloric acid; water; and mixtures of two or more thereof. The reaction is generally carried out at a temperature ranging from 0° C. to the boiling point of the solvent to be actually used. Reaction time varies depending on the type of a reduction method to be used, but the reaction may be completed within 24 hours.

Where the substituent $R^2$ in the formula (I) is a group other than the hydroxyl group, the corresponding compound may also be prepared by reacting a compound of the formula (III) with a compound of the formula (IV) in accordance with the following reaction scheme:

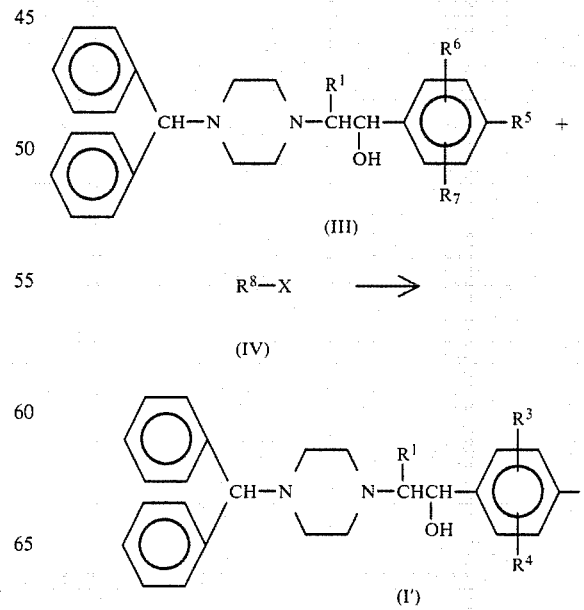

wherein $R^{2'}$ is an aralkyloxy group, a lower alkoxy group containing 1–5 carbon atoms or a lower alkenyloxy group containing 3–5 carbon atoms; $R^5$ is a hydroxyl group, an aralkyloxy group, a lower alkoxy group containing 1–5 carbon atoms or a lower alkenyloxy group containing 3–5 carbon atoms; $R^6$ is a hydrogen atom, or a hydroxyl group, an aralkyloxy group, a lower alkoxy group containing 1–5 carbon atoms or a lower alkenyloxy group containing 3–5 carbon atoms; $R^7$ is a hydrogen atom, or a hydroxyl group or a lower alkoxy group containing 1–5 carbon atoms; $R^8$ is an aralkyl group, a lower alkyl group containing 1–5 carbon atoms or a lower alkenyl group containing 3–5 carbon atoms; X is a reactive group; and $R^1$, $R^3$ and $R^4$ have the same significance as defined above, provided that at least one of $R^5$, $R^6$ and $R^7$ is a hydroxyl group; and $R^{2'}$ is a group other than the lower alkoxy group containing 1–5 carbon atoms when both $R^3$ and $R^4$ are hydrogen atoms.

In the compound of the formula (IV), the aralkyl, lower alkyl and lower alkenyl groups for $R^8$ correspond respectively to the aralkyloxy, lower alkoxy and lower alkenyloxy groups for each of $R^{2'}$, $R^3$ and $R^4$. In addition, as suitable reactive groups for X, use may be made of a halogen atom and alkoxy sulfonyloxy, p-toluenesulfonyloxy and methanesulfonyloxy groups.

The reaction between the compound (III) and the compound (IV) may be carried out in a manner known per se in the art, either in the absence of additives or in the presence of a basic substance such as sodium hydroxide, potassium carbonate, pyridine, triethylamine or the like. Any reaction solvent may be employed if it has no adverse effect on the reaction. Reaction temperature ranges preferably from 0° C. to the boiling point of the solvent to be used. Reaction time varies depending on the type of the compound (IV), but the reaction may be completed within 24 hours.

The piperazine derivative of the formula (I) may be converted to its corresponding salt by a method known per se in the art. Any salt may be formed if it is pharmaceutically acceptable. Eligible salts are those of hydrochloric acid, hydrobromic acid, sulfuric acid, phosphoric acid, citric acid, fumaric acid, maleic acid, tartaric acid, p-toluenesulfonic acid and like acids.

Where $R^1$ is a lower alkyl group in the formula (I), there exist both erythro and threo isomers as stereoisomers. Such stereoisomers should be considered to be within the scope of the compounds contemplated by the invention.

The vasodilating effects and toxicity rates of certain compounds (I) of this invention were tested, with the results shown below.

In these tests 12 inventive compounds were used together with 5 reference compounds.

Inventive Compounds

1: 2-(4-Diphenylmethylpiperazinyl)-1-(4-hydroxyphenyl)ethanol.monohydrochloride
2: dl-erythro-2-(4-Diphenylmethylpiperazinyl)-1-(4-hydroxyphenyl)propanol.½tartrate
3: dl-threo-2-(4-Diphenylmethylpiperazinyl)-1-(4-hydroxyphenyl)propanol.tartrate
4: 1-(4-Benzyloxyphenyl)-2-(4-diphenylmethylpiperazinyl)ethanol.monohydrochloride
5: 1-(2,4-Dibenzyloxyphenyl)-2-(4-diphenylmethylpiperazinyl)ethanol.monohydrochloride
6: dl-threo-1-(4-Benzyloxyphenyl)-2-(4-diphenylmethylpiperazinyl)propanol.dihydrochloride
7: 1-(2,4-Dimethoxyphenyl)-2-(4-diphenylmethylpiperazinyl)ethanol.dihydrochloride
8: 1-(3,4-Dimethoxyphenyl)-2-(4-diphenylmethylpiperazinyl)ethanol.dihydrochloride
9: 2-(4-Diphenylmethylpiperazinyl)-1-(2,3,4-trimethoxyphenyl)ethanol.dihydrochloride
10: 2-(4-Diphenylmethylpiperazinyl)-1-(3,4,5-trimethoxyphenyl)ethanol.monohydrochloride
11: 1-(4-Allyloxyphenyl)-2-(4-diphenylmethylpiperazinyl)ethanol.monohydrochloride
12: 1-(2-Allyloxy-4-methoxyphenyl)-2-(4-diphenylmethylpiperazinyl)ethanol.dihydrochloride Reference Compounds 1: 2-(4-Diphenylmethylpiperazinyl)-1-(2-hydroxyphenyl)ethanol.monohydrochloride
2: 2-(4-Diphenylmethylpiperazinyl)-1-phenylethanol.dihydrochloride
3: 2-(4-Diphenylmethylpiperazinyl)-1-methyl-1-phenylethanol.dihydrochloride
4: Bencyclane fumarate (commercially sold as a cerebral vasodilator)
5: Cinnarizine (commercially sold as a cerebral vasodilator)

Test 1: Peripheral Vasodilating Effect

Mongrel dogs of both sexes each weighing about 10 kg were anesthetized with sodium pentobarbital (35 mg/kg, i.v.). Artificial respiration was performed with room air. The vertebral blood flow and femoral blood flow were measured by an electromagnetic flowmeter (Nihon Koden, MF-27) with flow probes. The blood pressure and heart rate were measured at the same time. For intravenous administration of each compound (1 mg/kg), the cephalic vein was cannulated and the compound solution injected.

The test results are summarized in Table 1.

TABLE 1

| Compound | Dosage (mg/kg) i.v. | Percentage of vertebral blood flow increase (%) | Percentage of vertebral blood flow increase against percentage of femoral blood flow increase |
|---|---|---|---|
| Inventive compound 1 | 1 | 76 | 3.6 |
| Inventive compound 2 | 1 | 66 | 3.5 |
| Inventive compound 3 | 1 | 60 | 3.2 |
| Inventive compound 4(1) | 1 | 90 | 5.8 |
| Inventive compound 5(1) | 1 | 62* | 15.3 |
| Inventive compound 6(1) | 1 | 96 | 8.5 |
| Inventive compound 7 | 1 | 123 | 5.8 |
| Inventive compound 8 | 1 | 84 | 15.3 |
| Inventive compound 9(2) | 1 | 124 | 6.1 |
| Inventive compound | 1 | 95 | 4.6 |

TABLE 1-continued

| Compound | Dosage (mg/kg) i.v. | Percentage of vertebral blood flow increase (%) | Percentage of vertebral blood flow increase against percentage of femoral blood flow increase |
|---|---|---|---|
| Inventive compound 10 | 1 | 93 | 2.0 |
| Inventive compound 11[2] | 1 | 123 | 7.7 |
| Inventive compound 12 | 1 | 26 | 1.2 |
| Reference compound 1 | 1 | 25 | 1.3 |
| Reference compound 2 | 1 | 20 | 1.1 |
| Reference compound 3[2] | 1 | 67 | 2.9 |
| Reference compound 4[3] | 1 | 60 | 2.5 |
| Reference compound 5[3] | | | |

Note:
[1]In a dimethylsulfoxide solution
[2]In a distilled water solution
[3]In a physiological saline solution
Other compounds were tested in a 5% aqueous tartaric acid solution.
*The blood flow increased in two phases, and the thus increased blood blow lasted for 30 minutes.

Test 2: Platelet Anti-coagulating Effect

Male Wistar rats each having a body weight of about 300 g were orally administered with the test compounds. With the lapse of 3 hours after administration of the compound, each rate was anesthetized with ether, and the blood was collected from its abdominal vein. A 3.8% sodium citrate solution was used as an anticoagulant. The blood was centrifuged at 1,000 rpm for 10 minutes. The resultant platelet-rich plasma (PRP) was centrifuged for further 10 minutes at 3,000 rpm, thereby collecting a platelet-poor plasma (PPP).

ADP or collagen was added to the PRP obtained above to induce coagulation, and the thus coagulated platelets were measured by turbidimetry using a platelet aggregation tracer ("PAT-4A", tradename of Niko Kizai Kabushiki Kaisha, Japan). The coagulation inhibition percentage was determined by the following equation:

$$\text{Inhibition percentage} = \frac{B - A}{B} \times 100$$

A: Maximum percentage of coagulation when a compound was administered
B: Maximum percentage of coagulation when physiological saline was administered
The test results are shown in Tables 2-1 and 2-2.

TABLE 2-1

| Compound | Dosage (mg/kg) | Inhibition percentage (%) ADP (2.7 uM) | Collagen (17.4 ug/ml) |
|---|---|---|---|
| Inventive compound 1 | 250 | 28 | 25 |
| Inventive compound 2 | 250 | 16 | 17 |
| Reference compound | 250 | 0 | 0 |

TABLE 2-1-continued

| Compound | Dosage (mg/kg) | Inhibition percentage (%) ADP (2.7 uM) | Collagen (17.4 ug/ml) |
|---|---|---|---|
| 4 | | | |

TABLE 2-2

| Compound | Dosage (mg/kg) | Inhibition percentage (%) Collagen (6.25 ug/ml) |
|---|---|---|
| Inventive compound 1 | 200 | 81 |
| Inventive compound 2 | 200 | 40 |
| Inventive compound 9 | 200 | 90 |

Aspirin, which is known to have strong platelet anticoagulating activity, exhibits an inhibition of 99% against collagen in a dosage of 200 mg/kg.

Test 3: Acute Toxicity

Certain test compounds of the invention were administered orally to SD-strain female or male rats each having a body weight of 150 to 200 g of ddN-strain male mice each having a body weight of about 20 g. The animals were observed for 7 days to determine their $LD_{50}$ values. The test results are summarized in Table 3.

TABLE 3

| Compound | Animal | $LD_{50}$ (mg/kg) |
|---|---|---|
| Inventive compound 1 | rats | >2,000 |
| Inventive compound 2 | rats | >2,000 |
| Inventive compound 4 | mice | >2,000 |
| Inventive compound 5 | mice | >2,000 |
| Inventive compound 7 | mice | 350 |
| Inventive compound 8 | mice | 470 |
| Inventive compound 9 | mice | 1,230 |
| Inventive compound 10 | mice | >2,000 |
| Inventive compound 11 | mice | >2,000 |

As is apparent from the above test results, each compound of the invention possesses both vasodilating activity for peripheral vessels and platelet anti-coagulating activity and exhibits superior effects as compared with conventional cerebral circulation vasodilators.

The compound (I) of the invention may be applied either orally or non-orally. Exemplary preparation forms for oral administration include tablets, capsules, powders, granules and syrups. Preparation forms for administration other than the oral route include those for injection and the like. For the formulation of such preparations, conventional excipients, disintegrators, binders, lubricants, dyestuffs, diluents and the like may be suitably employed.

Eligible excipients are glucose and lactose, and starch, sodium alginate and the like may be used as eligible disintegrators. Eligible lubricants include magnesium stearate, paraffin sulfate, talc and the like. Eligible binders are dimethyl cellulose, gelatin, polyvinylpyrrolidone and the like. The dosage of such preparations is generally in the range of 50 to 400 mg per day for an adult, but may be increased or decreased depending on the age and conditions of each patient.

The above disclosure generally describes the present invention. A more complete understanding of the invention will be obtained by the following specific examples and reference examples which are provided for purposes of illustration only and are not construed as limiting to the invention.

Reference Example 1

2-(4-Diphenylmethylpiperazinyl)-1-(4-hydroxyphenyl)ethanone 2.52 g (10 mmol) of 1-diphenylmethylpiperazine and 1.11 g (11 mmol) of triethylamine were dissolved in 30 ml of isopropanol, followed by addition of a solution obtained by dissolving 2.15 g (10 mmol) of α-bromo-p-hydroxyacetophenone in 20 ml of isopropanol. The mixture was allowed to stand overnight at room temperature. Precipitated crystals were collected by filtration. The crystals were successively washed with isopropanol, water and isopropanol and then dried to give 3.27 g of crude crystals of 2-(4-diphenylmethylpiperazinyl)-1-(4-hydroxyphenyl)ethanone (yield: 84.6%).

IR absorption spectrum $\nu_{max}^{KBr}$: 3400, 1680 cm$^{-1}$
NMR spectrum (CDCl$_3$)δ: 2.2–2.8(8H, m,

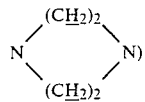

3.73(2H, s, CH$_2$C=O); 4.18(1H, s, ph$_2$CH); 6.7–7.9(14H, m, aromatic protons); 8.17(1H, s, OH)

Reference Example 2

(a)
1-(4-Benzyloxyphenyl)-2-(4-diphenylmethylpiperazinyl)ethanone

To 90 ml of an ethyl acetate solution containing 7.56 g (30 mmol) of 1-diphenylmethylpiperazine and 3.33 g (33 mmol) of triethylamine was added 9.15 g (30 mmol) of p-benzyloxy-α-bromoacetophenone. The resultant mixture was stirred at room temperature for 45 minutes. After addition of 100 ml of ice water, the thus obtained mixture was stirred for about 10 minutes. Precipitated crystals were collected by filtration and then washed successively with water, ethanol and ethyl acetate and thereafter dried to give 12.5 g of 1-(4-benzyloxyphenyl)-2-(4-diphenylmethylpiperazinyl)ethanone (yield: 87.4%).

Melting point: 151° C.
IR absorption spectrum $\nu_{max}^{KBr}$: 1685 cm$^{-1}$
NMR spectrum (CDCl$_3$)δ: 2.3–2.8(8H, m,

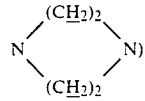

3.71(2H, s, CH$_2$C=O); 4.23(1H, s, ph$_2$CH); 5.07(2H, s, phCH$_2$O); 6.8–8.1(19H, m, aromatic protons)

(b)
2-(4-Diphenylmethylpiperazinyl)-1-(4-hydroxyphenyl)ethanone 12.5 g (26 mmol) of 1-(4-benzyloxyphenyl)-2-(4-diphenylmethyl-piperazinyl)ethanone and 2.8 g (26 mmol) of anisole were dissolved in a mixture of 37.5 ml of acetic acid and 12.5 ml of 47% hydrobromic acid. The resultant mixture was heated to reflux for 1 hour. After being cooled to room temperautre, the reaction mixture was washed with 200 ml of ether and then with 50 ml of ether to remove acetic acid. The resultant solution was neutralized with an aqueous 2N solution of sodium hydroxide. Separated organic substances were extracted with 120 ml of ethyl acetate and then washed with saturated saline. The ethyl acetate solution was dried over anhydrous sodium sulfate and then concentrated. The residue was taken up in 60 ml of isopropanol and allowed to stand at room temperature to give 6.28 g of crude crystals of 2-(4-diphenylmethylpiperazinyl)-1-(4-hydroxyphenyl)ethanone (yield: 62%).

Furthermore, the above crude crystals were dissolved in 25 ml of ethanol. After being incorporated with 0.9 equivalent of conc. hydrochloric acid, the resultant mixture was allowed to stand to cause a monohydrochloride salt to precipitate. The salt was converted to its corresponding free base. Repetition of the same operation as stated above gave 4.73 g of pure 2-(4-diphenylmethylpiperazinyl)-1-(4-hydroxyphenyl)ethanone monohydrochloride.

Reference Example 3

2-(4-Diphenylmethylpiperazinyl)-1-(4-hydroxyphenyl)-propanone

To a reflux solution containing 100 ml of chloroform, 12.6 g (50 mmol) of 1-diphenylmethylpiperazine and 5.62 g (55 mmol) of triethylamine was dropped over 2 hours a chloroform solution containing 12.7 g (55 mmol) of α-bromo-p-hydroxypropiophenone. The resultant mixture was heated to reflux for further one hour. After being cooled, the reaction mixture was concentrated, and the residue was added with 200 ml of ether. The residue was then washed first with water and then with saturated saline and dried over anhydrous sodium sulfate. The ether solution was concentrated, and the residue was subjected to silica gel column chromatography (silica gel 600 g; chloroform:methanol=100:1) to give 12.1 g of crude 2-(4-diphenylmethylpiperazinyl)-1-(4-hydroxyphenyl)propanone as a colorless oily substance (yield: 60%).

IR absorption spectrum $\nu_{max}^{neat}$: 3300, 1665 cm$^{-1}$
NMR spectrum (CDCl$_3$)δ: 1.26(3H, d, J=6 Hz, CH—CH$_3$); 2.3–2.8(8H, m,

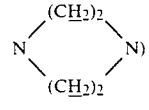

3.99(1H, q, J=6 Hz, CH—CH$_3$); 4.14(1H, s, ph$_2$CH) 6.43(1H, s, OH) 6.7–8.1(14H, m, aromatic protons)

Reference Example 4

(a)
1-4-(Benzyloxyphenyl)-2-(4-diphenylmethyl-piperazinyl)propanone 12.6 g (50 mmol) of 1-diphenylmethylpiperazine, 16.0 g (50 mmol) of p-benzyloxy-α-bromopropiophenone and 5.56 g (55 mmol) of triethylamine were heated to reflux for 2 hours in 100 ml of chloroform. After being cooled to room temperature, the resultant reaction mixture was washed first with water and then with saturated saline. The chloroform solution was dried over anhydrous sodium sulfate and concentrated to form crude crystals which were then recrystallized from methanol to 20.3 g of 1-(4-benzyloxyphenyl)-2-(4-diphenylmethyl-piperazinyl)propanone (yield: 83%).
Melting point: 107° C.
IR absorption spectrum $\nu_{max}^{KBr}$: 1680 cm$^{-1}$
NMR spectrum (CDCl$_3$)δ: 1.24(3H, d, J=7 Hz, CH—C$\underline{H}_3$); 2.24–2.72(8H, m,

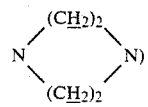

3.97(1H, q, J=7 Hz, C$\underline{H}$—CH$_3$); 4.18(1H, s, ph$_2$C$\underline{H}$); 5.10(2H, s, phC$\underline{H}_2$O); 6.97–8.11(19H, m, aromatic protons)

(b)
2-(4-Diphenylmethylpiperazinyl)-1-(4-hydroxyphenyl)-propanone 9.0 g (18 mmol) of 1-(4-benzyloxyphenyl)-2-(4-diphenylmethyl-piperazinyl)propanone was dissolved in 27 ml of hot acetic acid, and the resultant mixture was added with 13 ml of conc. hydrochloric acid. The reaction mixture was heated to reflux for 2.5 hours, cooled to room temperature and then added with 50 ml of ether. Precipitated crystals were collected by filtration and thoroughly washed with ether to give 8.6 g of crude crystals of 2-(4-diphenylmethylpiperazinyl)-1-(4-hydroxyphenyl)propanone dihydrochloride. To the crystals were added 30 ml of an aqueous 1N solution of sodium hydroxide and 100 ml of ethyl acetate. The resultant mixture was thoroughly stirred. An aqueous saturated solution of sodium hydrogen carbonate was then added with stirring to the above mixture until the latter turned to an alkaline state. The ethyl acetate layer was separated, washed successively with water and saturated saline and then dried over anhydrous sodium sulfate. Ethyl acetate was removed under reduced pressure to give 6.1 g of colorless, oily crude 2-(4-diphenylmethylpiperazinyl)-1-(4-hydroxyphenyl)propanone (yield: 85%).

Reference Example 5

2-(4-Diphenylmethylpiperazinyl)-1-(2,3,4-trimethoxyphenyl)ethanone

In 60 ml of isopropanol were taken up 11.9 g (47 mmol) of 1-diphenylmethylpiperazine and 5.23 g (52 mmol) of triethylamine, and the resultant mixture was added with a solution which had been prepared by dissolving 13.6 g (47 mmol) of 2-bromo-1-(2,3,4-trimethoxyphenyl)ethanone in 50 ml of isopropanol. After being stirred for 3 hours at room temperature, the reaction mixture was poured into 200 ml of water. The mixture was extracted with 150 ml of ethyl acetate. The thus obtained organic layer was washed successively with water and saturated saline and thereafter dried over anhydrous sodium sulfate. After removal of the solvent, the residue was recrystallized from ethanol to give 14.8 g of 2-(4-diphenylmethylpiperazinyl)-1-(2,3,4-trimethoxyphenyl)ethanone (yield: 68%).
Melting point: 119° C.
IR absorption spectrum $\nu_{max}^{KBr}$: 1680 cm$^{-1}$
NMR spectrum (CDCl$_3$)δ: 2.3–2.7(8h, m,

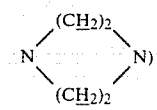

3.77(2H, s, C$\underline{H}_2$C=O); 3.84(3H, s, OCH$_3$); 3.85(3H, s, OCH$_3$); 3.95(3H, s, OC$\underline{H}_3$); 4.23(1$\underline{H}$, s, ph$_2$C$\underline{H}$); 6.5–7.5(12H, m, aromatic protons)

Incidentally, the carbonyl compounds, which were used as raw materials in Examples 5 and 7 to 9, were prepared in the same manner as in Reference Example 5.

Example 1

2-(4-Diphenylmethylpiperazinyl)-1-(4-hydroxyphenyl)ethanol

In 50 ml of methanol was dissolved 3.0 g (7.8 mmol) of 2-(4-diphenylmethylpiperazinyl)-1-(4-hydroxyphenyl)ethanone, to which 3.0 g (79 mmol) of sodium borohydride was added slowly under ice-cooled conditions. The reaction mixture was then stirred overnight at room temperature, and methanol was removed under reduced pressure. Thereafter, 100 ml of ether was added to the residue, and the solution was washed successively with water and saturated saline and dried over anhydrous sodium sulfate. The resultant ether solution was concentrated, and the residue was purified by silica gel column chromatography (silica gel 90 g; chloroform:methanol=100:1) to give 2.4 g of 2-(4-diphenylmethylpiperazinyl)-1-(4-hydroxyphenyl)ethanol (yield: 79%) which, upon recrystallization from a mixed solvent of ethyl acetate and n-hexane, gave white crystals.
Melting point: 154.5° C.
IR absorption spectrum $\nu_{max}^{KBr}$: 3400, 2820, 1620, 1600, 1510, 1450, 1250, 1150, 1005, 830, 750, 710 cm$^{-1}$
NMR spectrum(CDCl$_3$)δ: 2.2–2.9(10H, m,

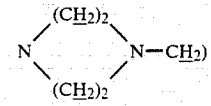

4.18(1H, s, ph$_2$C$\underline{H}$); 4.59(1H, t, j=7 Hz, C$\underline{H}$—OH); 5.50(2H, broad s, O$\underline{H}$×2); 6.5–7.5(14H, m, aromatic protons)

Elementary analysis (%): Calculated for C$_{25}$H$_{28}$N$_2$O$_2$: C, 77.29; H, 7.26; N, 7.21; Found: C, 77.09; H, 7.13; N, 7.22

To 112 ml of 1N hydrochloric acid was added 21.8 g (56.2 mmol) of 2-(4-diphenylmethylpiperazinyl)-1-(4-hydroxyphenyl)ethanol. The mixture was vigorously stirred at room temperature for 2 hours, and the resultant white solid was collected by filtration and washed with water. The white solid was then suspended in 80 ml of water and stirred with heating at 75° to 80° C. for 40 minutes. Suspended white crystals were collected by hot filtration, washed with water and then dried to give 22.0 g of 2-(4-diphenylmethylpiperazinyl)-1-(4-hydroxyphenyl)ethanol. monohydrochloride (yield: 92%).

Melting point: 214° C. (decomposed)

IR absorption spectrum $\nu_{max}^{KBr}$: 3400, 3260, 2820, 2670, 2590, 1615, 1510, 1450, 1265, 1215, 970, 830, 760, 705, 695 cm$^{-1}$

Example 2

2-(4-Diphenylmethylpiperazinyl)-1-(4-hydroxyphenyl)propanol

In 50 ml of methanol was dissolved 4.8 g (12 mmol) of 2-(4-diphenylmethylpiperazinyl)-1-(4-hydroxyphenyl)propanone, followed by portionwise addition of 5.0 g (132 mmol) of sodium borohydride under ice-cooled conditions. After completion of the reaction, 100 ml of water wad added to the reaction mixture, followed by extraction with ether. The ether extract was washed successively with water and saturated saline and then dried over anhydrous sodium sulfate. The ether solution was concentrated, and the residue was subjected to silica gel column chromatography (silica gel 130 g; chloroform:methanol=100:1) to give 1.44 g of dl-threo-2-(4-diphenylmethylpiperazinyl)-1-(4-hydroxyphenyl)propanol (yield: 30%) and 1.42 g of dl-erythro-2-(4-diphenylmethylpiperazinyl)-1-(4-hydroxyphenyl)propanol (yield: 29%). Either of the threo and erythro isomers was recrystallized from a mixed solvent of benzene and n-hexane.

Threo isomer

Melting point: 180° C.

IR absorption spectrum $\nu_{max}^{KBr}$: 3340, 2820, 1615, 1600, 1510, 1450, 1160, 1010, 830, 700 cm$^{-1}$ MMR spectrum (CDCl$_3$) δ: 0.60(3H, d, J=6 Hz, CH—CH$_3$); 2.1-2.8(9H, m,

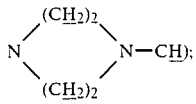

4.09(1H, d, J=10 Hz, CH—OH); 4.20 (1H, s, ph$_2$CH); 6.27(2H, broad s, OH×2); 6.9-7.5(14H, m, aromatic protons)

Elementary analysis (%): Calculated for C$_{26}$H$_{30}$N$_2$O$_2$: C, 77.58; H, 7.51; N, 6.96; Found: C, 77.85; H, 7.49; N, 7.05

Erythro isomer

Melting point: 118° C.

IR absorption spectrum $\nu_{max}^{KBr}$: 3380, 2830, 1620, 1605, 1515, 1450, 1150, 1000, 825, 710 cm$^{-1}$ NMR spectrum (CDCl$_3$)δ: 0.80(3H, d, J=6 Hz, CH—CH$_3$); 2.2-2.7(9H, m,

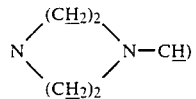

4.17(1H, s, ph$_2$CH); 4.77(1H, d, J=4 Hz, CH—OH); 5.09(2H, broad s, OH×2); 6.9-7.5(14H, m, aromatic protons)

Elementary analysis (%): Calculated for C$_{26}$H$_{30}$N$_2$O$_2$: C, 77.58; H, 7.51; N, 6.96; Found: C, 77.44; H, 7.51; N, 6.82

In 30 ml of hot acetone was dissolved 9.8 g (24 mmol) of dl-erythro-2-(4-diphenylmethylpiperazinyl)-1-(4-hydroxyphenyl)propanol. The solution was added to 30 ml of a hot acetone solution containing 1.9 g (13 mmol) of tartaric acid and slowly cooled to room temperature. Precipitated white crystals were collected by filtration and then dried to give 8.8 g of dl-erythro-2-(4-diphenylmethylpiperazinyl)-1-(4-hydroxyphenyl)propanol. ½ tartrate (yield: 76%).

Melting point: 201° C. (decomposed)

IR absorption spectrum $\nu_{max}^{KBr}$: 3370, 3030, 1600, 1510, 1490, 1450, 1365, 1270, 1240, 1200, 1120, 1085, 1040, 990, 840, 800, 760, 745, 705 cm$^{-1}$

Example 3

1-(4-Benzyloxyphenyl)-2-(4-diphenylmethylpiperazinyl)ethanol

In 24 ml of tetrahydrofuran was suspended 0.60 g (16 mmol) of lithium aluminum hydride, to which a suspension consisting of 24 ml of tetrahydrofuran and 3.0 g (6.3 mmol) of 1-(4-benzyloxyphenyl)-2-(4-diphenylmethylpiperazinyl)ethanone was added portionwise under ice-cooled conditions. After being stirred for 0.5 hour, the resultant mixture was added dropwise with 5 ml of ethyl acetate, followed by further addition of 50 ml of ethyl acetate. The thus prepared solution was poured into an aqueous solution of ammonium chloride, and the organic layer was separated. The organic layer was washed twice with saturated saline and then dried over anhydrous sodium sulfate. The solvent was removed, and the residue was recrystallized from a mixed solvent of ethanol and chloroform to give 2.37 g of 1-(4-benzyloxyphenyl)-2-(4-diphenylmethylpiperazinyl)ethanol (yield: 79%).

Melting point: 129° C.

IR absorption spectrum $\nu_{max}^{KBr}$: 3420, 3030, 2820, 1610, 1505, 1445, 1300, 1240, 1135, 1000, 820, 740, 690 cm$^{-1}$ NMR spectrum (CDCl$_3$) δ: 2.0-2.9(10H, m,

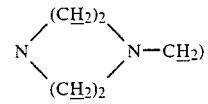

3.89(1H, broad s, OH); 4.21(1H, s, ph$_2$CH); 4.41(1H, t, J=7 Hz, CH—OH); 5.01(2H, s, OCH$_2$ph); 6.7-7.5(19H, m, aromatic protons)

Elementary analysis (%): Calculated for C$_{32}$H$_{34}$N$_2$O$_2$: C, 80.30; H, 7.16; N, 5.85; Found: C, 80.07; H, 7.11; N, 5.78

In 4.8 ml of acetone was dissolved 0.48 g (1 mmol) of the above free base, followed by addition of 0.083 ml of conc. hydrochloric acid and by further addition of 5 ml of ether to give 0.33 g of 1-(4-benzyloxy-phenyl)-2-(4-diphenylmethylpiperazinyl)ethanol.monohydrochloride as white crystals (yield: 64%).

Melting point: 187° C. (decomposed)

IR absorption spectrum $\nu_{max}^{KBr}$: 3240, 2820, 1610, 1505, 1445, 1250, 1170, 1075, 1030, 970, 830, 735, 705 cm$^{-1}$

Example 4 dl-threo-1-(4-Benzyloxyphenyl)-2-(4-diphenylmethylpiperazinyl)propanol

The procedure of Example 3 was repeated except that 1-(4-benzyloxyphenyl)-2-(4-diphenylmethylpiperazinyl)propanone was employed. The crude reaction product was subjected to silica gel column chromatography and then recrystallized from a mixed solvent of chloroform and isopropanol to give dl-threo-1-(4-benzyloxyphenyl)-2-(4-diphenylmethylpiperazinyl)-propanol (yield: 70%).

Melting point: 157° C.

IR absorption spectrum $\nu_{max}^{KBr}$: 3380, 2810, 1610, 1505, 1445, 1380, 1240, 1160, 1010, 840, 745, 700 cm$^{-1}$ NMR spectrum (CDCl$_3$) δ: 0.76(3H, d, J=7 Hz, C$\underline{H}_3$); 2.1-2.9(9H, m,

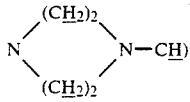

4.13(1H, d, J=10 Hz, C$\underline{H}$—OH); 4.23(1H, s, ph$_2$C$\underline{H}$); 5.01(2H, s, OC$\underline{H}_2$ph); 6.7-7.5 (14H, m, aromatic protons)

Elementary analysis(%): Calculated for C$_{33}$H$_{36}$N$_2$O$_2$: C, 80.45; H, 7.37; N, 5.69; Found: C, 80.42; H, 7.58; N, 5.72

In 2.5 ml of methylene chloride was dissolved 0.25 g (0.5 mmol) of the above free base, into which hydrogen chloride gas was blown. After removal of the solvent, 5 ml of ether was added to give 0.23 g of dl-threo-1-(4-benzyloxyphenyl)-2-(4-diphenylmethylpiperazinyl)-propanol.dihydrochloride as white crystalline powder (yield: 81%).

Melting point: 205° C. (decomposed)

IR absorption spectrum $\nu_{max}^{KBr}$: 3360, 3260, 1610, 1500, 1450, 1250, 1170, 1010, 750, 700, 690 cm$^{-1}$

Example 5

2-(4-Diphenylmethylpiperazinyl)-1-(3,4,5-trimethoxyphenyl)ethanol

A similar procedure to Example 3 was followed using 2-(4-diphenylmethylpiperazinyl)-1-(3,4,5-trimethoxyphenyl)ethanone. The crude reaction product was subjected to silica gel column chromatography and then recrystallized from ethanol to give 2-(4-diphenylmethyl-piperazinyl)-1-(3,4,5-trimethoxyphenyl)ethanol (yield: 77%).

Melting point: 173° C.

IR absorption spectrum $\nu_{max}^{KBr}$: 3420, 2940, 2820, 1595, 1490, 1450, 1325, 1230, 1125, 1000, 875, 705 cm$^{-1}$ NMR spectrum (CDCl$_3$)δ: 2.0-2.9 (10H, m,

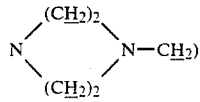

3.80(3H, s, OC$\underline{H}_3$); 3.83(6H, s, OC$\underline{H}_3$×2); 4.22(1H, s, ph$_2$C$\underline{H}$); 4.60(1$\underline{H}$, m, C$\underline{H}$—OH); 6.5-7.6(12H, m, aromatic protons)

Elementary analysis(%): Calculated for C$_{28}$H$_{34}$N$_2$O$_4$: C 72.70; H, 7.41; N, 6.06; Found: C, 72.48; H, 7.62; N, 5.89

In 15 ml of acetone was dissolved with heating 0.92 g (2 mmol) of the above free base, followed by addition of 2 ml of a 1N acetone solution of hydrogen chloride and by further addition of 10 ml of ether. The mixture was stirred at room temperature for 2 hours to give 0.86 g of 2-(4-diphenylmethylpiperazinyl)-1-(3,4,5-trimethoxyphenyl)ethanol.monohydrochloride as white crystals (yield: 86%).

Melting point: 222° C. (decomposed)

IR absorption spectrum $\nu_{max}^{KBr}$: 3320, 2940, 2830, 1595, 1445, 1325, 1230, 1120, 1005, 900, 750, 700 cm$^{-1}$

Example 6

2-(4-Diphyenylmethylpiperazinyl)-1-(2,3,4-trimethoxyphenyl)ethanol 13.8 g (30 mmol) of 2-(4-diphenylmethylpiperazinyl)-1-(2,3,4-trimethoxyphenyl)ethanone was dissolved in a mixed solvent consisting of 100 ml of ethanol and 30 ml of chloroform, followed by addition of 2.27 g (60 mmol) of sodium borohydride under ice-cooled conditions over 20 minutes. The resultant mixture was stirred at room temperature for 2 hours, followed by addition of 50 ml of an aqueous saturated solution of ammonium chloride and by further addition of 100 ml of water. The resultant mixture was extracted with 200 ml of ethyl acetate, and the organic layer was successively washed with water and saturated saline and then dried over anhydrous sodium sulfate. The solvent was removed, and the residue was recrystallized from a mixed solvent of chloroform and ethanol to give 9.70 g of 2-(4-diphenylmethylpiperazinyl)-1-(2,3,4-trimethoxyphenyl)ethanol as white crystals (yield: 70%).

Melting point: 128° C.

IR absorption spectrum $\nu_{max}^{KBr}$: 3420, 2940, 2805, 1600, 1485, 1460, 1420, 1270, 1140, 1100, 1020, 1000, 745, 700 cm$^{-1}$ NMR spectrum (CDCl$_3$)δ: 2.2-3.0(10H, m,

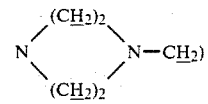

3.90(3H, s, OC$\underline{H}_3$); 3.92(3H, s, OC$\underline{H}_3$); 3.94(3H, s, OC$\underline{H}_3$); 4.21(1H, s, ph$_2$C$\underline{H}$); 4.94(1H, dd, J=8 Hz, J=4 Hz, C$\underline{H}$—OH); 6.5-7.5(12H, m, aromatic protons)

Elementary analysis(%): Calculated for C$_{28}$H$_{34}$N$_2$O$_4$: C, 72.70, H, 7.41; N, 6.06; Found: C, 72.48; H, 7.60; N, 5.86

2.31 g (5 mmol) of the above free base was dissolved with heating in 23 ml of acetone, followed by addition of 10 ml of a 1N acetone solution of hydrogen chloride to give 2.19 g of 2-(4-diphenylmethylpiperazinyl)-1-(2,3,4,-trimethoxyphenyl)ethanol.dihydrochloride as white crystalline powder (yield: 82%).

Melting point: 189° C. (decomposed)

IR absorption spectrum $\nu_{max}^{KBr}$: 3250, 2940, 2420, 1600, 1490, 1450, 1420, 1280, 1195, 1095, 1015, 750, 710 cm$^{-1}$

EXAMPLE 7

1-(2,4-Dibenzyloxyphenyl)-2-(4-diphenylmethylpiperazinyl)ethanol

In a mixed solvent consisting of 50 ml of ethanol and 20 ml of chloroform was dissolved 4.80 g (8.2 mmol) of 1-(2,4-dibenzyloxyphenyl)-2-(4-diphenylmethyl-pieperazinyl)ethanone, to which 580 mg (16.6 mmol) of sodium borohydride was added under ice-cooled conditions over 30 minutes. The resultant mixture was stirred with ice-cooling for one hour and at room temperature for further one hour. Precipitated white crystals were collected by filtration and then recrystallized from a mixed solvent of chloroform and ethanol to give 3.00 g of 1-(2,4-dibenzyloxyphenyl)-2-(4-diphenylmethylpiperazinyl)ethanol (yield: 63%).

Melting point: 151° C.

IR absorption spectrum $\nu_{max}^{KBr}$: 3450, 2810, 1610, 1585, 1495, 1445, 1375, 1290, 1175, 1130, 1030, 1000, 825, 730, 700 cm$^{-1}$ NMR spectrum (CDCl$_3$)δ: 2.2–2.9(10H, m,

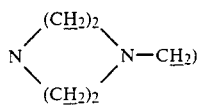

3.74(1H, broad s, O$\underline{H}$); 4.21(1H, s, ph$_2$C$\underline{H}$); 5.00(4H, s, phC$\underline{H}_2$×2); 5.10(1H, t, J=6 Hz, C$\underline{H}$—OH); 6.4–6.7(2H, m,

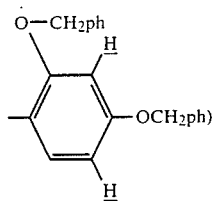

7.0–7.5(21H, m, other aromatic protons)

Elementary analysis(%): Calculated for C$_{39}$H$_{40}$N$_2$O$_3$: C, 80.11; H, 6.90; N, 4.79; Found: C, 79.86; H, 6.84; N, 4.51

The above free base was converted to its hydrochloric acid salt in the same manner as in Example 6. The salt was recrystallized from a mixed solvent of ethanol and water to give 1-(2,4-dibenzyloxyphenyl)-2-(4-diphenylmethylpiperazinyl)ethanol.monohydrochloride (yield: 70%).

Melting point: 195° C. (decomposed)

IR absorption spectrum $\nu_{max}^{KBr}$: 3250, 1610, 1585, 1495, 1450, 1380, 1295, 1170, 1125, 1025, 1010, 740, 730, 700 cm$^{-1}$

EXAMPLE 8

1-(2,4-Dimethoxyphenyl)-2-(4-diphenylmethylpiperazinyl)ethanol

The procedure of Example 6 was followed using 1-(2,4-dimethoxyphenyl)-2-(4-diphenylmethylpiperazinyl)ethanone. The crude reaction product was subjected to silica gel column chromatography and then recrystallized from ethanol to give 1-(2,4-dimethoxyphenyl)-2-(4-diphenylmethylpiperazinyl)ethanol (yield: 73%).

Melting point: 116° C.

IR absorption spectrum $\nu_{max}^{KBr}$: 3180, 2940, 2820, 1610, 1590, 1495, 1450, 1290, 1205, 1150, 1135, 1040, 1000, 830, 700 cm$^{-1}$ NMR spectrum (CDCl$_3$)δ: 2.2–3.0(10H, m,

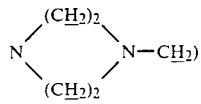

3.76(3H, s, OC$\underline{H}_3$) 3.77(3H, s, OC$\underline{H}_3$) 4.23(1H, s, ph$_2$C$\underline{H}$) 5.01(1H, dd, J=8 Hz, J=4 Hz, C$\underline{H}$—OH) 6.3–6.6(2H, m,

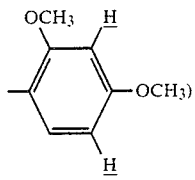

7.0–7.5(11H, m, other aromatic protons)

Elementary analysis(%): Calculated for C$_{27}$H$_{32}$N$_2$O$_3$: C, 74.97; H, 7.46; N, 6.48; Found: C, 74.88; H, 7.43; N, 6.56

The above free base was converted to its hydrochloric acid salt in the same manner as in Example 6, and the resultant salt was recrystallized from ethanol to give 1-(2,4-dimethoxyphenyl)-2-(4-diphenylmethylpiperazinyl)ethanol.dihydrochloride (yield: 60%).

Melting point: 178° C. (decomposed)

IR absorption spectrum $\nu_{max}^{KBr}$: 3270, 2940, 2850, 2250, 1615, 1595, 1500, 1450, 1300, 1210, 1160, 1070, 1035, 925, 820, 755, 705 cm$^{-1}$

EXAMPLE 9

1-(3,4-Dimethoxyphenyl)-2-(4-diphenylmethylpiperazinyl)ethanol

The procedure of Example 6 was repeated except that 1-(3,4-dimethoxyphenyl)-2-(4-diphenylmethylpiperazinyl)ethanone was employed. The crude reaction product was subjected to silica gel column chromatography and then recrystallized from ethanol to give 1-(3,4-dimethoxyphenyl)-2-(4-diphenylmethylpiperazinyl)ethanol (yield: 75%).

Melting point: 85° C.

IR absorption spectrum $\nu_{max}^{KBr}$: 3400, 2820, 1600, 1510, 1450, 1265, 1235, 1140, 1030, 860, 760, 705 cm$^{-1}$ NMR spectrum (CDCl$_3$)δ: 2.2–2.9(10H, m,

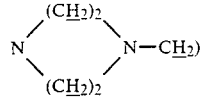

3.83(3H, s, OC$\underline{H}_3$); 3.86(3H, s, OC$\underline{H}_3$); 4.21(1H, s, ph$_2$C$\underline{H}$); 4.61(1H, t, J=7 Hz, C$\underline{H}$—OH); 6.7–7.5(13H, m, aromatic protons)

Elementary analysis(%): Calculated for C$_{27}$H$_{32}$N$_2$O$_3$: C, 74.97; H, 7.46; N, 6.48; Found: C, 75.19; H, 7.62; N, 6.68

The above free base was converted to its hydrochloric acid salt in the same manner as in Example 6, and the salt was recrystallized from a mixed solvent of ethanol and ether to give 1-(3,4-dimethoxyphenyl)-2-(4-diphenylmethylpiperazinyl)ethanol.dihydrochloride (yield: 74%).

Melting point: 175° C. (decomposed)

IR absorption spectrum $\nu_{max}^{KBr}$: 3360, 2950, 2550, 1600, 1505, 1450, 1260, 1230, 1160, 1140, 1020, 755, 700 cm$^{-1}$

EXAMPLE 10

1-(4-Allyloxyphenyl)-2-(4-diphenylmethylpiperazinyl)ethanol

In 1.2 liters of ethanol were dissolved 120 g (0.31 mol) of 2-(4-diphenylmethylpiperazinyl)-1-(4-hydroxyphenyl)-ethanol, 74.8 g (0.62 mol) of allyl bromide and 41 g of potassium hydroxide. The resultant solution was heated with refluxing for one hour. After cooling the solution and then removing the solvent, the residue was added with 1.0 liter of ethyl acetate. The resultant mixture was washed successively with an aqueous 1N solution of sodium hydroxide, water and saturated saline, followed by drying over anhydrous sodium sulfate. The solvent was removed, and the residue was crystallized from a mixed solvent of ethanol and n-hexane to give 84.6 g of 1-(4-allyloxyphenyl)-2-(4-diphenylmethyl-piperazinyl)ethanol (yield: 64%).

Melting point: 100° C.

IR absorption spectrum $\nu_{max}^{KBr}$: 3380, 2940, 2810, 1610, 1505, 1445, 1240, 1140, 1000, 920, 825, 760, 705 cm$^{-1}$ NMR spectrum (CDCl$_3$)δ: 2.0-2.9 (10H, m,

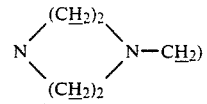

3.90(1H, broad s, OH); 4.20(1H, s, ph$_2$CH); 4.47(2H, m, OCH$_2$); 4.60(1H, t, J=5 Hz, CH—OH);

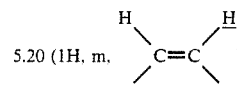

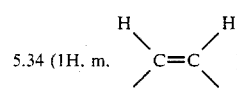

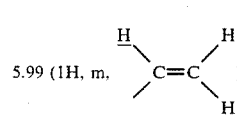

6.6-7.6(14H, m, aromatic protons)

Elementary analysis(%): Calculated for C$_{26}$H$_{30}$N$_2$O$_2$: C, 78.47; H, 7.53; N, 6.54; Found: C, 78.75; H, 7.70; N, 6.55

The procedure of Example 6 was followed to give 1-(4-allyloxyphenyl)-2-(4-diphenylmethylpiperazinyl)ethanol.monohydrochloride from the above free base (yield: 79%).

Melting point: 192° C. (decomposed)

IR absorption spectrum $\nu_{max}^{KBr}$: 3280, 2560, 1610, 1505, 1445, 1420, 1235, 1170, 1080, 1010, 825, 705 cm$^{-1}$

EXAMPLE 11

1-(2-Allyloxy-4-methoxyphenyl)-2-(4-diphenylmethyl-piperazinyl)ethanol 53 mg (2.2 mmol) of sodium hydride was suspended in 5 ml of tetrahydrofuran. To the resultant suspension was added a solution which had been prepared by dissolving 837 mg (2 mmol) of 2-(4-diphenylmethyl-piperazinyl)-1-(2-hydroxy-4-methoxyphenyl)ethanol in 5 ml of tetrahydrofuran under ice-cooled conditions. Thereafter, 2 ml of a tetrahydrofuran solution of 266 mg (2.2 mmol) of allylbromide was added and heated with refluxing for 4 hours. After being cooled to room temperature, the resultant mixture was added with 50 ml of ethyl acetate. The mixture was then washed successively with water and saturated saline and then dried over anhydrous sodium sulfate. The solvent was removed, and the residue was subjected to thin-layer chromatography to give 419 mg of 1-(2-allyloxy-4-methoxyphenyl)-2-(4-diphenylmethylpiperazinyl)ethanol as a colorless oily substance (yield: 46%).

IR absorption spectrum $\nu_{max}^{KBr}$: 3420, 2940, 2810, 1610, 1590, 1490, 1450, 1290, 1250, 1200, 1160, 1135, 1040, 1005, 925, 830, 745, 705 cm$^{-1}$ NMR spectrum (CDCl$_3$)δ: 2.3-2.9(10H, m,

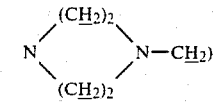

3.62(1H, s, OH); 3.75(3H, s, OCH$_3$); 4.21(1H, s, ph$_2$CH); 4.47(2H, m, OCH$_2$); 5.05(1H, dd, J=8 Hz, J=4 Hz, CH—OH);

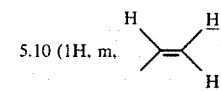

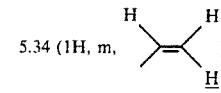

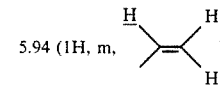

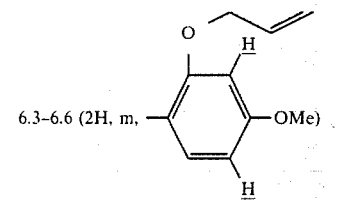

7.0-7.5(11H, m, other aromatic protons)

The above free base was converted to its hydrochloric acid salt in the same manner as in Example 6. The salt was then recrystallized from ethanol to give 1-(2-allyloxy-4-methoxyphenyl)-2-(4-diphenylmethyl-piperazinyl)ethanol.dihydrochloride (yield: 56%).

Melting point: 170° C. (decomposed)

IR absorption spectrum $\nu_{max}^{KBr}$: 3240, 2940, 2280, 1605, 1585, 1490, 1435, 1290, 1200, 1160, 1060, 1015, 920, 815, 750, 700 cm$^{-1}$ Elementary analysis(%): Calculated for C$_{29}$H$_{36}$Cl$_2$N$_2$O$_3$: C, 65.53; H, 6.83; N, 5.27; Found: C, 65.63; H, 6.84; N, 5.00

EXAMPLE 12

Example of Dosable Preparation (Tablets)

The following components were contained in each tablet (220 mg):

| Effective component | 50 mg |
| --- | --- |
| Lactose | 100 mg |
| Starch | 50 mg |
| Magnesium stearate | 5 mg |
| Hydroxypropylcellulose | 15 mg |

EXAMPLE 13

Example of Dosable Preparation (Capsules)

The following components were contained in each hard gelatin capsule (350 mg):

| | |
|---|---|
| Effective component | 40 mg |
| Lactose | 200 mg |
| Starch | 70 mg |
| Polyvinylpyrrolidone | 5 mg |
| Crystalline cellulose | 35 mg |

EXAMPLE 14

Example of Dosable Preparation (Granules)

The following components were contained in each gram of granules:

| | |
|---|---|
| Effective component | 200 mg |
| Lactose | 450 mg |
| Corn starch | 300 mg |
| Hydroxypropylcellulose | 50 mg |

Having now fully described the invention, it will be apparent to one of ordinary skill in the art that many changes and modifications can be made thereto without departing from the spirit or scope of the invention as set forth herein.

What is claimed is:

1. A compound represented by the formula:

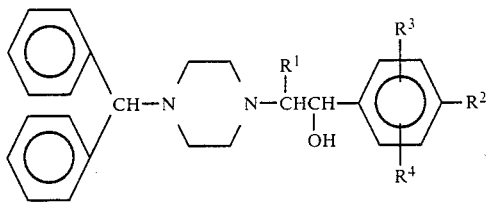

wherein $R^1$ is a hydrogen atom or a lower alkyl group; $R^2$ is a hydroxyl group, or a phenyl substituted lower alkoxy group, a lower alkoxy group having 1–5 carbon atoms or a lower alkenyloxy group having 3–5 carbon atoms; $R^3$ is a hydrogen atom, or a phenyl substituted lower alkoxy group, a lower alkoxy group having 1–5 carbon atoms or a lower alkenyloxy group having 3–5 carbon atoms; and $R^4$ is a hydrogen atom or a lower alkoxy group having 1–5 carbon atoms, provided that $R^2$ is a group other than the lower alkoxy group having 1–5 carbon atoms when both $R^3$ and $R^4$ are hydrogen atoms; or a pharmaceutically acceptable salt thereof.

2. A process for preparing a piperazine derivative represented by the formula (I):

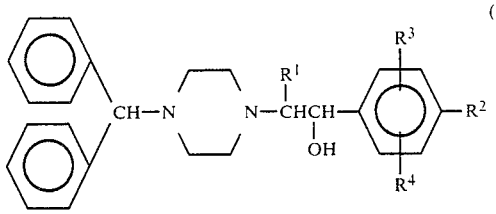

wherein $R^1$ is a hydrogen atom or a lower alkyl group; $R^2$ is a hydroxyl group, or an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^2$ is a group other than the lower alkoxy group containing 1–5 carbon atoms when both $R^3$ and $R^4$ are hydrogen atoms; or a pharmaceutically acceptable salt thereof, which process comprises reducing a compound represented by the formula (II):

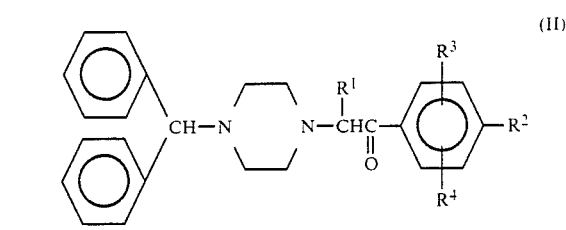

wherein $R^1$, $R^2$, $R^3$ and $R^4$ have the same significance as defined above, and if desired, converting the piperazine derivative to the corresponding salt by a method known per se.

3. A process for preparing a piperazine derivative represented by the formula (I'):

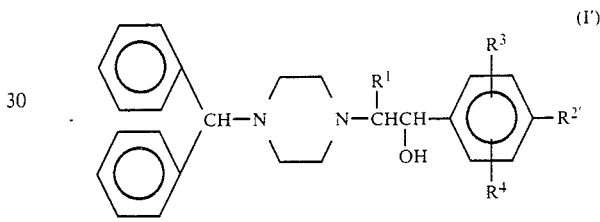

wherein $R^1$ is a hydrogen atom or a lower alkyl group; $R^{2'}$ is an aralkyloxy group, a lower alkoxy group containing 1–5 carbon atoms or a lower alkenyloxy group containing 3–5 carbon atoms; $R^3$ is a hydrogen atom, or an aralkyloxy group, a lower alkoxy group containing 1–5 carbon atoms or a lower alkenyloxy group containing 3–5 carbon atoms; and $R^4$ is a hydrogen atom or a lower alkoxy group containing 1–5 carbon atoms, provided that $R^{2'}$ is a group other than the lower alkoxy group containing 1–5 carbon atoms when both $R^3$ and $R^4$ are hydrogen atoms; or a pharmaceutically acceptable salt thereof, which process comprises reacting a compound represented by the formula (III):

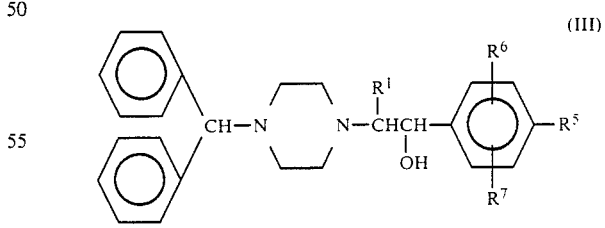

wherein $R^1$ is a hydrogen atom or a lower alkyl group; $R^5$ is a hydroxyl group, an aralkyloxy group, a lower alkoxy group containing 1–5 carbon atoms or a lower alkenyloxy group containing 3–5 carbon atoms; $R^6$ is a hydrogen atom, or a hydroxyl group, an aralkyloxy group, a lower alkoxy group containing 1–5 carbon atoms or a lower alkenyloxy group containing 3–5 carbon atoms; and $R^7$ is a hydrogen atom, or a hydroxyl group or a lower alkoxy group containing 1–5 carbon atoms, provided that at least one of $R^5$, $R^6$ and $R^7$ is a hydroxyl group, with a compound represented by the formula (IV):

$$R^8-X \quad (IV)$$

wherein $R^8$ is an aralkyl group, a lower alkyl group containing 1-5 carbon atoms or a lower alkenyl group containing 3-5 carbon atoms; and X is a reactive group, and if desired, converting the piperazine derivative to the corresponding salt by a method known per se.

4. A cerebral circulation-improving drug dose having as the effective component a therapeutically effective amount of a compound represented by the formula:

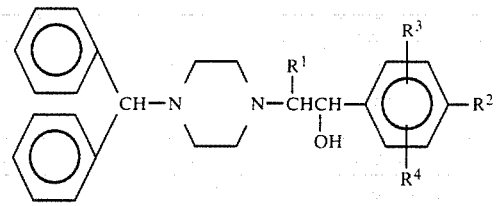

wherein $R^1$ is a hydrogen atom or a lower alkyl group; $R^2$ is a hydroxyl group or a phenyl substituted lower alkoxy group, a lower alkoxy group having 1-5 carbon atoms, or a lower alkenyloxy group having 3-5 carbon atoms; $R^3$ is a hydrogen atom, or a phenyl substituted lower alkoxy group, a lower alkoxy group having 1-5 carbon atoms or a lower alkenyloxy group having 3-5 carbon atoms; and $R^4$ is a hydrogen atom or a lower alkoxy group having 1-5 carbon atoms, provided that $R^2$ is a group other than the lower alkoxy group having 1-5 carbon atoms when both $R^3$ and $R^4$ are hydrogen atoms; or a pharmaceutically acceptable salt thereof and a pharmaceutically acceptable carrier or diluent.

5. A method of improving cerebral circulation in mammals which comprises administering to a mammal a therapeutically effective amount of the compound of claim 1.

* * * * *